United States Patent
Janka et al.

(10) Patent No.: US 9,493,395 B2
(45) Date of Patent: Nov. 15, 2016

(54) PRODUCTION OF TWO ESTERS USING HOMOGENEOUS CATALYST

(71) Applicant: Eastman Chemical Company, Kingsport, TN (US)

(72) Inventors: Mesfin Ejerssa Janka, Kingsport, TN (US); Robert Thomas Hembre, Johnson City, TN (US); Stephanie Rollins Testerman, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/680,595

(22) Filed: Apr. 7, 2015

(65) Prior Publication Data
US 2016/0297741 A1 Oct. 13, 2016

(51) Int. Cl.
C07C 67/00 (2006.01)
C07C 67/44 (2006.01)

(52) U.S. Cl.
CPC ................... *C07C 67/44* (2013.01)

(58) Field of Classification Search
CPC ............... C07C 67/44; A01B 12/006
See application file for complete search history.

(56) References Cited

FOREIGN PATENT DOCUMENTS

| JP | 08-099933 | * | 4/1996 |
|----|-----------|---|--------|
| JP | 08-099933 | A | 4/1996 |
| JP | 08-119904 | A | 5/1996 |

OTHER PUBLICATIONS

"933" (JP08-099933, 1996).*
933 (JP08-099933, 1996).*
Menashe et al.; "Catalytic Disproportionation of Aldehydes with Ruthenium Complexes;" Organometallics; 1991; 10; pp. 3885-3891.
Seki et al.; "The Tishchenko Reaction: A Classic and Practical Tool for Ester Synthesis;" Chemistry Letters; vol. 35; No. 8 (2006); pp. 824-829.
PCT International Search Report and the Written Opinion of the International Searching Authority with Date of Mailing Jun. 14, 2014 for International Application No. PCT/US2016/024609.
Trost et al.; "Butenolide Synthesis Based upon a Contra-Electronic Addition in a Ruthenium-Catalyzed Alder Ene Reaction. Synthesis and Absolute Configuration of (+)-Ancepsenolide"; J. Am. Chem. Soc.; 1994, 116; pp. 4985-4986.
Blum et al.; "H-Transfer Catalysis With $Ru_3(CO)_{12}$"; Tetrahedron Letters; vol. 22; No. 16; 1981; pp. 1541-1544.
Simon et al.; "An in situ Generated Ruthenium Catalyst for the Tishchenko Reaction"; Adv. Synth. Catal.; 2010; 352; pp. 305-308.
De Joarder et al.; "Enantioselective synthesis of a potential 1,5-syn-poly C1-C24 subunit of (−)-caylobolide A"; Tetrahedron Letters; 54; 2013; pp. 5826-5829.
Murahashi et al.; "Ruthenium-Catalyzed Oxidative Transformation of Alcohols and Aldehydes to Esters and Lactones"; J. Org. Chem.; 1987; 52; pp. 4319-4327.
Ooi et al.; "Practical Oppenauer (OPP) Oxidation of Alcohols with a Modified Aluminum Catalyst"; Organic Letters; 2002; vol. 4; No. 16; pp. 2669-2672.

* cited by examiner

*Primary Examiner* — Yevegeny Valenrod
*Assistant Examiner* — Blaine G Doletski

(57) ABSTRACT

Disclosed is a process for preparing two esters by reacting an aldehyde with an alcohol in the presence of a ruthenium complex compound as a catalyst. The process is particularly useful for preparing ethyl acetate and n-butyl acetate, isobutyl acetate, or 2-ethylhexyl acetate in high yield by coupling acetaldehyde with n-butanol, i-butanol, or 2-ethylhexanol.

27 Claims, No Drawings

PRODUCTION OF TWO ESTERS USING HOMOGENEOUS CATALYST

FIELD OF THE INVENTION

The invention generally relates to a catalytic process for preparing two esters by reacting an aldehyde with an alcohol.

BACKGROUND OF THE INVENTION

Discovered more than one hundred years ago, the Tishchenko reaction is an atom-efficient method for synthesizing esters from aldehydes. Lewis acids, metal alkoxides, and late transition metal catalysts have been used to catalyze this reaction.

Today, the Tishchenko reaction is commonly employed to make simple esters, i.e., those produced by the disproportionation of a single aldehyde (homo-coupling). If two different aldehydes are coincidentally subjected to Tishchenko reaction conditions, a near statistical mixture of four possible esters are produced—two from "homo-coupling" and two from "cross-coupling" as shown in Equation (1):

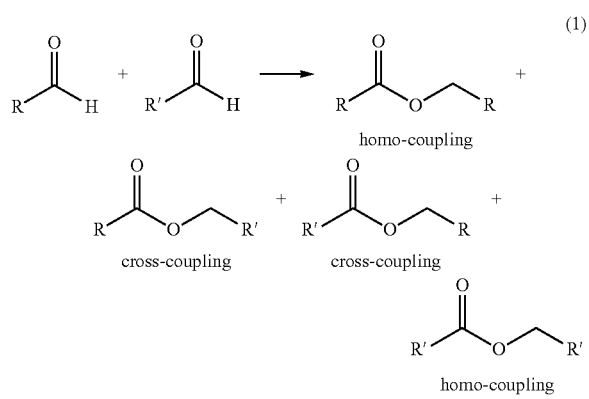

A significant limitation of this technology is that there are no selective catalysts for a crossed-Tishchenko reaction between two different aldehydes to make two esters in high yield.

Thus, there is a need for a crossed-Tischenko type reaction that can selectively produce two esters in high yield and selectivity.

The present invention addresses this need as well as others, which will become apparent from the following description and the appended claims.

SUMMARY OF THE INVENTION

The invention is as set forth in the appended claims.

Briefly, the present invention provides a process for preparing two ester compounds. The process comprises contacting an aldehyde with an alcohol at an aldehyde-to-alcohol molar ratio of greater than 1:1 and up to 25:1 in the presence of a ruthenium complex compound at conditions effective to produce two ester compounds. The process is capable of high conversions of the starting aldehyde, e.g., of at least 50%. The process can generate two ester compounds at a combined selectivity of, e.g., at least 50%.

The present invention also provides a process for preparing ethyl acetate and n-butyl acetate, isobutyl acetate, or 2-ethylhexyl acetate. The process comprises contacting acetaldehyde with an alcohol selected from n-butanol, i-butanol, or 2-ethylhexanol at an aldehyde-to-alcohol molar ratio of greater than 1:1 to 25:1 in the presence of a ruthenium complex compound at conditions effective to produce ethyl acetate and n-butyl acetate, isobutyl acetate, or 2-ethylhexyl acetate.

DETAILED DESCRIPTION OF THE INVENTION

It has been surprisingly discovered that by coupling an aldehyde with an alcohol via a crossed-Tischenko type reaction, catalyzed by a homogenous catalyst, two esters can be selectively produced in very high yields, as shown in Equation (2):

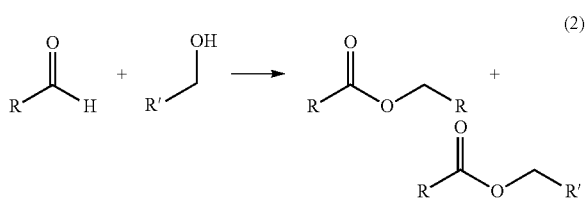

Thus, the present invention provides a process for preparing two ester compounds. The process comprises contacting an aldehyde with an alcohol at an aldehyde-to-alcohol molar ratio of greater than 1:1 and up to 25:1 in the presence of a ruthenium complex compound at conditions effective to produce two ester compounds.

The aldehydes and alcohols useful in the process of the invention are not particularly limiting. For example, they may have 1 to 12 carbon atoms, which may be straight-chain, branched, alicyclic, or aromatic. Preferred aldehydes include acetaldehyde, and preferred alcohols include n-butanol, i-butanol, and 2-ethylhexanol.

Likewise, esters that can be prepared from the process of the invention are not particularly limiting. For example, the ester products may have 2 to 24 carbon atoms, which may also be straight-chain, branched, alicyclic, or aromatic. Preferred ester products include ethyl acetate and n-butyl acetate, isobutyl acetate, or 2-ethylhexyl acetate.

The process of the invention is performed with an aldehyde-to-alcohol molar ratio of greater than 1:1 and up to 25:1. It is preferred to use an excess of aldehyde in order maximize selectivity to the two desired esters and to minimize formation of by-products. Other preferred aldehyde-to-alcohol molar ratios include 2:1 to 25:1, 3:1 to 25:1, 4:1 to 25:1, 8:1 to 25:1, 12:1 to 25:1, 16:1 to 25:1, 2:1 to 24:1, 3:1 to 24:1, 4:1 to 24:1, 8:1 to 24:1, 12:1 to 24:1, 16:1 to 24:1, 2:1 to 20:1, 3:1 to 20:1, 4:1 to 20:1, 8:1 to 20:1, 12:1 to 20:1, 16:1 to 20:1, 2:1 to 16:1, 3:1 to 16:1, 4:1 to 16:1, 8:1 to 16:1, and 12:1 to 16:1.

In the process of the present invention, a ruthenium complex compound (RuCC) is used as a catalyst. Any RuCC having esterification capability for producing esters from an aldehyde and an alcohol may be used.

By "ruthenium complex compound" or "RuCC," it is meant a complex compound containing one or more ruthenium atoms and one or more ligands linked by direct metal-ligand bonding. The formal oxidation number of the ruthenium atom, and the type and quantity of groups serving as the ligand are not particularly limiting. Examples of such ligands include carbon monoxide, phosphines, hydrides, and substituted cyclopentadienones. Substituted cyclopentadienones are preferred ligands.

Specific examples of RuCCs include $H_2Ru(PPh_3)_4$, $Ru_3(CO)_{12}$, $(Ph_4C_4CO)Ru(CO)_3$, $[(4-ClC_6H_4)_4C_4CO]Ru(CO)_3$, $[2,5-(C_6H_4)_2-3,4-(4-MeOC_6H_4)_2C_4CO]Ru(CO)_3$, $[2,5-(C_6H_4)_2-3,4-(4-FC_6H_4)_2C_4CO]Ru(CO)_3$, $(Ph_4C_4CO)_2H(\mu-H)(CO)_4Ru_2$, $[(4-ClC_6H_4)_4C_4CO]_2H(\mu-H)(CO)_4Ru_2$, $[2,5-(C_6H_4)_2-3,4-(4-MeOC_6H_4)_2C_4CO]_2H(\mu-H)(CO)_4Ru_2$, and $[2,5-(C_6H_4)_2-3,4-(4-FC_6H_4)_2C_4CO]_2H(\mu-H)(CO)_4Ru_2$. These compounds can be synthesized using well-known methods (e.g., N. Menashe et al., *Organometallics*, Vol. 10, p. 3885 (1991)).

The preferred catalyst is $(Ph_4C_4CO)2H(\mu-H)(CO)_4Ru_2$. It is known in the literature as Shvo's catalyst and is sometimes written as $[Ru_2(CO)_4(\mu-H)(C_4Ph_4COHOCC_4Ph_4)]$. Shvo's catalyst is a cyclopentadienone-ligated diruthenium complex having the structure 1:

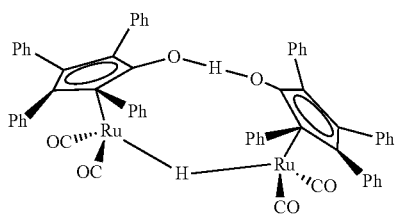

The amount of catalyst used can range from $10^{-7}:1$ to $1:1$ (molar ratio) with respect to the aldehyde, and preferably ranges from $10^{-3}:1$ to $0.01:1$ (molar ratio).

After the reaction, the catalyst can be separated from the products by distillation, extraction, adsorption, or other ordinary methods, and reused.

The process of the present invention can be carried out without a solvent. But if the RuCC has low solubility in the reaction medium comprising the aldehyde and the alcohol, the reaction can be carried out in a suitable solvent in order to dissolve the RuCC, or as otherwise needed. Examples of suitable solvents include hydrocarbons such as hexane, benzene, and toluene; ethers such as diethyl ether, dimethoxyethane, tetrahydrofuran, and dioxanes; and esters such as ethyl acetate, butyl acetate, and 2-ethylhexyl acetate.

The reaction is typically carried out by introducing the aldehyde, the alcohol, and the catalyst into a vessel, and then mixing the contents. The reaction temperature can range from 0 to 200° C., from 20 to 150° C., or 20 to 100° C.

The reaction pressure and atmosphere are not particularly limiting. The reaction may be carried out at less than atmospheric pressure, at atmospheric pressure, or at elevated pressure. The reaction is preferably carried out in an inert atmosphere, such as nitrogen or argon.

The reaction time depends on the reaction temperature, but typically can range, for example, from 0.1 to 10 hours, or from 0.5 to 3 hours.

The reaction can be carried out in the absence of an added hydrogen acceptor. Examples of hydrogen acceptors include α,β-unsaturated carbonyl compounds such as mesityl oxide, methyl vinyl ketone, and benzalacetone; ketones such as acetone and cyclohexanone; disubstituted acetylenes such as diphenylacetylene; and esters of pyruvic acid, phenylglyoxylic acid, and other α-keto acids.

The process of the invention can be used to prepare ethyl acetate and n-butyl acetate, isobutyl acetate, or 2-ethylhexyl acetate. Acetaldehyde can be contacted with an alcohol selected from n-butanol, i-butanol, or 2-ethylhexanol at an aldehyde-to-alcohol molar ratio of greater than 1:1 and up to 25:1 in the presence of a ruthenium complex compound at conditions effective to produce ethyl acetate and n-butyl acetate, isobutyl acetate, or 2-ethylhexyl acetate.

The process of the invention is capable of converting the acetaldehyde at a degree of conversion of at least 50%, or at least 70%, or at least 80%, or at least 90%, or at least 95%. The degree of conversion is determined by the following equation:

$$\text{Conversion} = \frac{\text{moles of aldehyde consumed}}{\text{moles of aldehyde fed}} \times 100.$$

The process of the invention is capable of selectively generating two esters at a combined degree of selectivity of at least 50%, or at least 70%, or at least 80%, or at least 90%, or at least 95%. The combined degree of selectivity of two esters is determined according the following equation:

Combined Selectvity=Selectivity of Ester 1+Selectivity of Ester 2

The composition comprising all reaction products of the process desirably contains no more than 20 mole % of alcohol product(s), or no more than 15 mole % of alcohol product(s), or no more than 10 mole % of alcohol product(s), or no more than 5 mole % of alcohol product(s), or no more than 2 mole % of alcohol product(s).

The composition comprising all reaction products of the process desirably contains no more than 20 mole % of undesired ester product(s), or no more than 15 mole % of undesired ester product(s), or no more than 10 mole % of undesired ester product(s), or no more than 5 mole % of undesired ester product(s), or no more than 2 mole % of undesired ester product(s).

The composition comprising all reaction products of the process desirably contains no more than 20 mole % of any compound other than two esters, or no more than 15 mole % of any compound other than two esters, or no more than 10 mole % of any compound other than two esters, or no more than 5 mole % of any compound other than two esters, or no more than 2 mole % of any compound other than two esters.

The process of the invention can produce ethyl acetate and n-butyl acetate at a combined selectivity of at least 80%, and optionally can have a degree of conversion of the aldehyde of at least 90%.

The process of the invention can produce ethyl acetate and iso-butyl acetate at a combined selectivity of at least 80%, and optionally can have a degree of conversion of the aldehyde of at least 90%.

The process of the invention can produce ethyl acetate and 2-ethylhexyl acetate at a combined selectivity of at least 80%, and optionally can have a degree of conversion of the aldehyde of at least 90%.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

As used herein, the indefinite articles "a" and "an" mean one or more, unless the context clearly suggests otherwise. Similarly, the singular form of nouns includes their plural form, and vice versa, unless the context clearly suggests otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Abbreviations

Below is a list of structures and abbreviations of the compounds used or produced in the following examples.

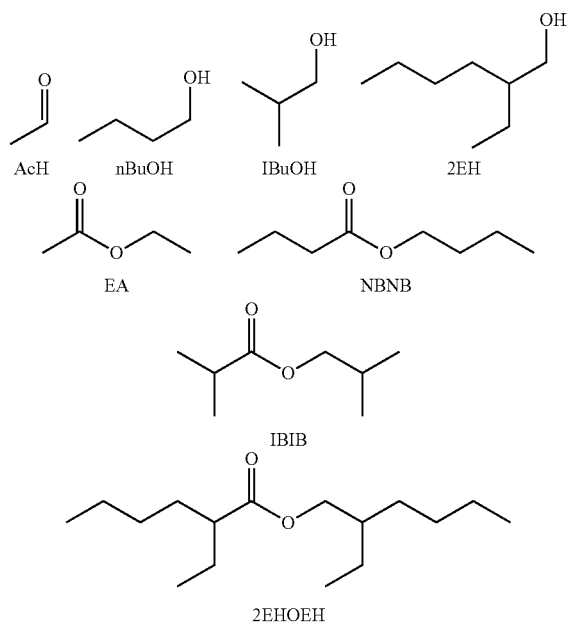

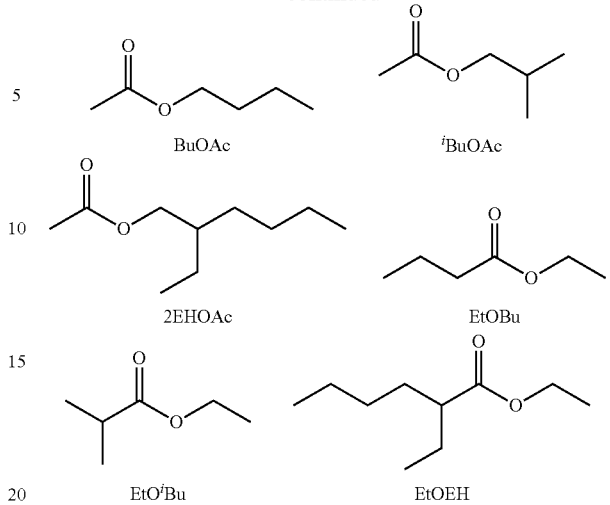

Materials n-Butanol, isobutanol, 2EH, toluene, and acetaldehyde were purchased from Aldrich. Shvo's catalyst was obtained from Stem Chemicals Inc.

Gas Chromatographic Method

Samples were analyzed using a Shimadzu 2010 gas chromatograph equipped with a split/splitless heated injection port (60:1 split ratio, 300° C.) and a Flame Ionization Detector (300° C.), and a 60 meter 0.32 mm I.D. 1 μm film thickness DB-1301 capillary column. Helium was the carrier gas and was run at a constant linear velocity of 20.0 cm/sec throughout the method. The column oven program was a total of 20.00 min and began at a temperature of 45° C. (held for 1.00 min) and was ramped at a rate of 25.00° C./min up to 200.0° C. Samples were prepared by weighing approximately 1.000 g of sample into a vial and then adding 10 mL of internal standard solution (BuCN in ACN). The vial was then mixed well and an aliquot was transferred to a GC vial. EZChrom Elite chromatography data system was used to process the results.

Selectivity Calculations

Selectivities were calculated based on moles of components in the recovered product.

% Selectivity of $EA$=[2*mol of $EA$/(2*mol of $EA$+mol of BuOAc+mol of EtOH+mol of EtOBu+mol of NBNB or IBIB or 2EHOEH+ mol of $AA$)]*100.

% Selectivity of BuOAc=[mol of BuOAc/(2*mol of $EA$+mol of BuOAc+mol of EtOH+mol of EtOBu+mol of NBNB or IBIB or 2EHOEH+ mol of $AA$)]*100.

% Selectivity of EtOH=[mol of EtOH/(2*mol of $EA$+mol of BuOAc+mol of EtOH+mol of EtOBu+mol of NBNB or IBIB or 2EHOEH+ mol of $AA$)]*100.

% Selectivity of EtOBu=[mol of EtOH/(2*mol of $EA$+mol of BuOAc+mol of EtOH+mol of EtOBu+mol of NBNB or IBIB or 2EHOEH+ mol of $AA$)]*100.

Example 1

A 50-mL autoclave was charged with 7.0 g (159 mmol) of AcH, 0.50 g (7 mmol) of n-butanol, 0.18 g (0.2 mmol) of Shvo's catalyst, and 14.6 g of toluene. The autoclave was pressurized with 200 psig of argon and was heated to 80° C. under continuous argon flow. It was kept at reaction temperature for 1 h, cooled to room temperature, and depressurized. The liquid product was analyzed by gas chromatography. Conversion and selectivity data are given in Table 1.

Example 2

A 50-mL three-neck flask equipped with a condenser, a thermocouple, and argon purge line was charged with 7.0 g (159 mmol) of AcH, 1.5 g (7 mmol) of n-butanol, 0.65 g (0.6 mmol) of Shvo's catalyst, and 14.6 g of toluene. The flask was heated to 60° C. under continuous argon flow. It was kept at reaction temperature for 1 h, then cooled to room temperature. The liquid product was analyzed by gas chromatography. Conversion and selectivity data are given in Table 1.

Example 3

A 50-mL three-neck flask equipped with a condenser, a thermocouple, and argon purge line was charged with 7.0 g (159 mmol) of AcH, 3.0 g (40 mmol) of n-butanol, 0.72 g (0.7 mmol) of Shvo's catalyst, and 14.6 g of toluene. The flask was heated to 60° C. under continuous argon flow. It was kept at reaction temperature for 1 h, then cooled to room temperature. The liquid product was analyzed by gas chromatography. Conversion and selectivity data are given in Table 1.

TABLE 1

Crossed-Tischenko Type Reaction of AcH and n-BuOH

| Ex. | AcH to n-BuOH Feed Mole Ratio | Temp. (° C.) | % AcH Conv. | % Selectivity | | | | |
|---|---|---|---|---|---|---|---|---|
| | | | | EA | BuOAc | EtOH | EtOBu | NBNB |
| 1[a] | 23.6 | 80 | >99.9 | 91 | 7.4 | 1.4 | 0.2 | 0 |
| 2[b] | 7.9 | 60 | 98.4 | 82.2 | 14.4 | 3.3 | 0.2 | 0 |
| 3[b] | 4 | 60 | 99.6 | 64.7 | 25.4 | 9.4 | 0.5 | 0.1 |

[a]0.33 mol % catalyst loading.
[b]0.10 mol % catalyst loading.

Example 4

A 50-mL autoclave was charged with 7.0 g (158.6 mmol) of AcH, 0.50 g (6.7 mmol) of i-butanol, 0.18 g (0.17 mmol) of Shvo's catalyst, and 14.6 g of toluene. The autoclave was pressurized with 200 psig of argon and was heated to 80° C. under continuous argon flow. It was kept at reaction temperature for 1 h, cooled to room temperature, and depressurized. The liquid product was analyzed by gas chromatography. Conversion and selectivity data are given in Table 2.

Example 5

A 50-mL three neck flask equipped with a condenser, a thermocouple, and argon purge line was charged with 7.0 g (159 mmol) of AcH, 1.5 g (7 mmol) of i-butanol, 0.65 g (0.6 mmol) of Shvo's catalyst, and 14.6 g of toluene. The flask was heated to 60° C. under continuous argon flow. It was kept at reaction temperature for 1 h, then cooled to room temperature. The liquid product was analyzed by gas chromatography. Conversion and selectivity data are given in Table 2.

Crossed-Tischenko Type Reaction of AcH and i-BuOH

| Ex. | AcH to i-BuOH Feed Mole Ratio | Temp. (° C.) | % AcH Conv. | % Selectivity | | | | |
|---|---|---|---|---|---|---|---|---|
| | | | | EA | BuOAc | EtOH | EtOBu | IBNB |
| 4[a] | 23.6 | 80 | >99.9 | 91.5 | 5.9 | 1.2 | 0.07 | 0 |
| 5[b] | 7.9 | 60 | 99.8 | 71.7 | 13.2 | 5.5 | 0.1 | 0 |

[a]0.33 mol % catalyst loading.
[b]0.10 mol % catalyst loading.

Example 6

A 50-mL autoclave was charged with 7.0 g (159 mmol) of AcH, 0.88 g (7 mmol) of 2EH, 0.18 g (0.2 mmol) of Shvo's catalyst, and 14.6 g of toluene. The autoclave was pressurized with 200 psig of argon and was heated to 80° C. under continuous argon flow. It was kept at reaction temperature for 1 h, then cooled to 23° C., and depressurized. The liquid product was analyzed by gas chromatography. Conversion and selectivity data are given in Table 3.

Example 7

A 50-mL autoclave was charged with 7.0 g (159 mmol) of AcH, 1.36 g (10 mmol) of 2EH, 0.183 g (0.2 mmol) of Shvo's catalyst, and 14.6 g of toluene. The autoclave was pressurized with 200 psig of argon and was heated to 80° C. under continuous argon flow. It was kept at reaction temperature for 1 h, cooled to room temperature, and depressurized. The liquid product was analyzed by gas chromatography. Conversion and selectivity data are given in Table 3.

Crossed-Tischenko Type Reaction of AcH and 2EH

| Ex. | AcH to 2EH Feed Mole Ratio | Temp. (° C.) | % AcH Conv. | % Selectivity | | | | |
|---|---|---|---|---|---|---|---|---|
| | | | | EA | BuOAc | EtOH | EtOBu | 2EH-OEH |
| 6[a] | 23.6 | 80 | >99.9 | 89.7 | 7.5 | 2.9 | 0 | 0 |
| 7[b] | 15.2 | 60 | >99.10 | 81.7 | 12.03 | 5.3 | 0 | 0 |

[a]0.33 mol % catalyst loading.
[b]0.10 mol % catalyst loading.

From Examples 1-7 above, it can be seen that the coupling of acetaldehyde with n-butanol, i-butanol or 2-EH alcohol proceeded cleanly to completion in less than 1 h. These examples revealed the excellent activity and selectivity of Shvo's catalyst for selective production of two esters. The ethanol co-product, formed by transesterification of ethyl acetate with the reactant alcohol, increased as the amount of the alcohol reactant in the feed increased.

The invention has been described in detail with particular reference to preferred embodiments thereof, but it will be understood that variations and modifications can be effected within the spirit and scope of the invention.

We claim:

1. A process for preparing two ester compounds, comprising:
   contacting an aldehyde with an alcohol at an aldehyde-to-alcohol molar ratio of greater than 2:1 and up to 25:1 in the presence of a ruthenium complex compound at conditions effective to produce two ester compounds.

2. The process according to claim 1, wherein the aldehyde-to-alcohol molar ratio ranges from 4:1 to 25:1.

3. The process according to claim 1, wherein the aldehyde-to-alcohol molar ratio ranges from 8:1 to 25:1.

4. The process according to claim 1, wherein the aldehyde-to-alcohol molar ratio ranges from 12:1 to 25:1.

5. The process according to claim 1, wherein the ruthenium complex compound comprises $[Ru_2(CO)_4(\mu\text{-H})(C_4Ph_4COHOCC_4Ph_4)]$.

6. The process according to claim 1, which is carried out in the absence of a hydrogen acceptor.

7. The process according to claim 1, wherein the aldehyde and the alcohol contain 1 to 12 carbon atoms.

8. The process according to claim 7, wherein the aldehyde comprises acetaldehyde.

9. The process according to claim 7, wherein the alcohol comprises n-butanol, i-butanol, or 2-ethylhexanol.

10. The process according to claim 7, wherein the two ester compounds comprise (a) ethyl acetate and (b) n-butyl acetate, isobutyl acetate, or 2-ethylhexyl acetate.

11. The process according to claim 1, which has an aldehyde conversion of at least 95%.

12. The process according to claim 1, which has a combined selectivity for the two ester compounds of at least 80%.

13. The process according to claim 1, which has a combined selectivity for the two ester compounds of at least 90%.

14. The process according to claim 1, which has a combined selectivity for the two ester compounds of at least 95%.

15. A process for preparing ethyl acetate and n-butyl acetate, isobutyl acetate, or 2-ethylhexyl acetate, the process comprising:
   contacting acetaldehyde with an alcohol selected from n-butanol, i-butanol, or 2-ethylhexanol at an aldehyde-to-alcohol molar ratio of greater than 2:1 and up to 25:1 in the presence of a ruthenium complex compound at conditions effective to produce ethyl acetate and n-butyl acetate, isobutyl acetate, or 2-ethylhexyl acetate.

16. The process according to claim 15, wherein the aldehyde-to-alcohol molar ratio ranges from 4:1 to 25:1.

17. The process according to claim 15, wherein the aldehyde-to-alcohol molar ratio ranges from 8:1 to 25:1.

18. The process according to claim 15, wherein the aldehyde-to-alcohol molar ratio ranges from 12:1 to 25:1.

19. The process according to claim 15, wherein the ruthenium complex compound comprises $[Ru_2(CO)_4(\mu\text{-H})(C_4Ph_4COHOCC_4Ph_4)]$.

20. The process according to claim 15, which is carried out in the absence of a hydrogen acceptor.

21. The process according to claim 15, which has an aldehyde conversion of at least 95%.

22. The process according to claim 15, which produces ethyl acetate and n-butyl acetate.

23. The process according to claim 22, which has a combined selectivity for ethyl acetate and n-butyl acetate of at least 80%.

24. The process according to claim 15, which produces ethyl acetate and isobutyl acetate.

25. The process according to claim 24, which has a combined selectivity for ethyl acetate and isobutyl acetate of at least 80%.

26. The process according to claim 15, which produces ethyl acetate and 2-ethylhexyl acetate.

27. The process according to claim 26, which has a combined selectivity for ethyl acetate and 2-ethylhexyl acetate of at least 80%.

* * * * *